United States Patent
Thomas et al.

(10) Patent No.: US 8,030,062 B2
(45) Date of Patent: *Oct. 4, 2011

(54) MICROFABRICATED APPARATUS FOR CELL BASED ASSAYS

(75) Inventors: Nicholas Thomas, Radyr Cardiff (GB); Per Andersson, Uppsala (SE)

(73) Assignee: Gyros Patent AB, Uppsala (SE)

( * ) Notice: Subject to any disclaimer, the term of this patent is extended or adjusted under 35 U.S.C. 154(b) by 121 days.

This patent is subject to a terminal disclaimer.

(21) Appl. No.: 12/236,120

(22) Filed: Sep. 23, 2008

(65) Prior Publication Data

US 2009/0239292 A1 Sep. 24, 2009

Related U.S. Application Data

(63) Continuation of application No. 10/650,412, filed on Aug. 28, 2003, now abandoned, which is a continuation of application No. 09/673,169, filed as application No. PCT/GB99/00954 on Mar. 17, 1999, now Pat. No. 6,632,656.

(30) Foreign Application Priority Data

Apr. 27, 1998 (GB) .................................. 9808836.2

(51) Int. Cl.
*C12M 1/34* (2006.01)

(52) U.S. Cl. ................ 435/288.5; 435/288.7; 435/297.5; 422/415; 422/72; 422/506

(58) Field of Classification Search ................ 435/288.5, 435/297.2, 297.5; 422/415, 72, 506
See application file for complete search history.

(56) References Cited

U.S. PATENT DOCUMENTS

| | | |
|---|---|---|
| 3,679,367 A | 7/1972 | Negersmith |
| 4,018,652 A | 4/1977 | Lanham et al. |
| 4,077,845 A | 3/1978 | Johnson |
| 4,154,793 A | 5/1979 | Guigan |
| 4,318,994 A | 3/1982 | Meyer et al. |
| 4,381,291 A | 4/1983 | Ekins et al. |

(Continued)

FOREIGN PATENT DOCUMENTS

DE 4400955 A1 6/1995

(Continued)

OTHER PUBLICATIONS

Ahn et al., "A fully integrated micromachined magnetic particle manipulator and separator," Microelectronics Research Center, School of Electrical and Computer Engineering, Georgia Institute of Technology, Atlanta, GA; pp. 91-96, 1994.

(Continued)

*Primary Examiner* — William H Beisner
(74) *Attorney, Agent, or Firm* — Fulbright & Jaworski L.L.P.

(57) ABSTRACT

Apparatus and methods are provided for performing cell growth and cell based assays in a liquid medium. The apparatus comprises a base plate supporting a plurality of micro-channel elements, each micro-channel element comprising a cell growth chamber, an inlet channel and an outlet channel, a cover plate positioned over the base plate to define the chambers and connecting channels. Means are incorporated in the cell growth chambers, for cell attachment and cell growth. In particular, the invention provides a rotatable disc microfabricated for performing cell growth and cell based assays. The apparatus and method can be used for the growth of cells and the detection and measurement of variety of biochemical processes and products using non-invasive techniques, that is techniques which do not compromise the integrity or viability of cells.

19 Claims, 2 Drawing Sheets

U.S. PATENT DOCUMENTS

| | | |
|---|---|---|
| 4,426,451 A | 1/1984 | Columbus |
| 4,440,638 A | 4/1984 | Judy et al. |
| 4,515,889 A | 5/1985 | Klose et al. |
| 4,661,451 A | 4/1987 | Hansen |
| 4,676,274 A | 6/1987 | Brown |
| 4,676,952 A | 6/1987 | Edelmann et al. |
| 4,729,862 A | 3/1988 | Salatiello et al. |
| 4,745,072 A | 5/1988 | Ekins et al. |
| 4,756,884 A | 7/1988 | Hillman et al. |
| 4,762,683 A | 8/1988 | Romanauskas |
| 4,839,292 A | 6/1989 | Cremonese |
| 4,868,129 A | 9/1989 | Gibbons et al. |
| 4,917,865 A | 4/1990 | Romanauskas |
| 4,940,527 A | 7/1990 | Kazlauskas et al. |
| 4,946,795 A | 8/1990 | Gibbons et al. |
| 5,006,749 A | 4/1991 | White |
| 5,122,284 A | 6/1992 | Braynin et al. |
| 5,160,702 A | 11/1992 | Kopf-Sill et al. |
| 5,171,695 A | 12/1992 | Ekins |
| 5,173,262 A | 12/1992 | Burtis et al. |
| 5,190,879 A | 3/1993 | Wolfe et al. |
| 5,230,866 A | 7/1993 | Shartle et al. |
| 5,242,803 A | 9/1993 | Burtis et al. |
| 5,252,294 A | 10/1993 | Kroy et al. |
| 5,304,487 A | 4/1994 | Wilding et al. |
| 5,368,704 A | 11/1994 | Madou et al. |
| 5,376,252 A | 12/1994 | Ekstrom et al. |
| 5,409,665 A | 4/1995 | Burd |
| 5,413,732 A | 5/1995 | Buhl et al. |
| 5,426,032 A | 6/1995 | Phillips et al. |
| 5,432,009 A | 7/1995 | Tabata et al. |
| 5,472,603 A | 12/1995 | Schembri |
| 5,587,128 A | 12/1996 | Wilding et al. |
| 5,593,838 A | 1/1997 | Zanzucchi et al. |
| 5,627,041 A | 5/1997 | Shartle |
| 5,635,358 A | 6/1997 | Wilding et al. |
| 5,637,469 A | 6/1997 | Wilding et al. |
| 5,650,334 A | 7/1997 | Zuk et al. |
| 5,653,939 A | 8/1997 | Hollis et al. |
| 5,660,993 A | 8/1997 | Cathey et al. |
| 5,690,841 A | 11/1997 | Elderstig |
| 5,698,162 A | 12/1997 | Belly et al. |
| 5,773,488 A | 6/1998 | Allmer et al. |
| 5,798,215 A | 8/1998 | Cathey et al. |
| 5,800,778 A | 9/1998 | Chen et al. |
| 5,912,134 A | 6/1999 | Shartle |
| 5,962,081 A | 10/1999 | Ohman |
| 5,992,820 A | 11/1999 | Fare et al. |
| 5,995,209 A | 11/1999 | Ohman et al. |
| 6,074,827 A | 6/2000 | Nelson et al. |
| 6,113,768 A | 9/2000 | Fuhr et al. |
| 6,126,765 A | 10/2000 | Ohman |
| 6,130,098 A | 10/2000 | Handique et al. |
| 6,143,247 A | 11/2000 | Sheppard, Jr. et al. |
| 6,143,248 A | 11/2000 | Kellogg et al. |
| 6,144,447 A | 11/2000 | Ohman |
| 6,192,768 B1 | 2/2001 | Wallman |
| 6,203,291 B1 | 3/2001 | Stemme et al. |
| 6,271,040 B1 | 8/2001 | Buechler |
| 6,296,020 B1 | 10/2001 | McNeely et al. |
| 6,299,839 B1 | 10/2001 | Karunaratne et al. |
| 6,319,468 B1 | 11/2001 | Sheppard, Jr. et al. |
| 6,319,469 B1 | 11/2001 | Mian et al. |
| 6,322,682 B1 | 11/2001 | Arvidsson et al. |
| 6,375,871 B1 | 4/2002 | Bentsen et al. |
| 6,379,929 B1 | 4/2002 | Burns et al. |
| 6,454,970 B1 | 9/2002 | Ohman et al. |
| 6,499,499 B2 | 12/2002 | Dantsker et al. |
| 6,591,488 B1 | 7/2003 | Tachibana |
| 6,591,852 B1 | 7/2003 | McNeely et al. |
| 6,620,478 B1 | 9/2003 | Ohman et al. |
| 6,632,656 B1 | 10/2003 | Thomas |
| 6,653,625 B2 | 11/2003 | Andersson et al. |
| 6,717,136 B2 | 4/2004 | Andersson et al. |
| 6,728,644 B2 | 4/2004 | Bielik et al. |
| 6,811,736 B1 | 11/2004 | Ohman et al. |
| 6,812,456 B2 | 11/2004 | Andersson et al. |
| 6,812,457 B2 | 11/2004 | Andersson et al. |
| 6,852,851 B1 | 2/2005 | Kenrick et al. |
| 6,878,555 B2 | 4/2005 | Andersson et al. |
| 6,884,370 B2 | 4/2005 | Ohman et al. |
| 6,884,395 B2 | 4/2005 | Andersson et al. |
| 6,919,058 B2 | 7/2005 | Andersson et al. |
| 6,955,738 B2 | 10/2005 | Derand et al. |
| 6,967,101 B1 | 11/2005 | Larsson et al. |
| 6,985,672 B2 | 1/2006 | Andersson et al. |
| 6,990,290 B2 | 1/2006 | Andersson et al. |
| 6,992,181 B2 | 1/2006 | Tooke et al. |
| 6,992,278 B2 | 1/2006 | Sjoberg et al. |
| 7,104,517 B1 | 9/2006 | Derand et al. |
| 7,148,476 B2 | 12/2006 | Andersson et al. |
| 7,323,345 B1 | 1/2008 | Stjernstrom et al. |
| 2002/0025583 A1 | 2/2002 | Ellsworth et al. |
| 2002/0125135 A1 | 9/2002 | Larsson et al. |
| 2002/0150512 A1 | 10/2002 | Kellogg et al. |
| 2003/0029724 A1 | 2/2003 | Derand et al. |
| 2003/0044322 A1 | 3/2003 | Andersson et al. |
| 2003/0047823 A1 | 3/2003 | Ohman et al. |
| 2003/0053934 A1 | 3/2003 | Andersson et al. |
| 2003/0054563 A1 | 3/2003 | Ljungstrom et al. |
| 2003/0064004 A1 | 4/2003 | Agren et al. |
| 2003/0066959 A1 | 4/2003 | Andersson et al. |
| 2003/0082075 A1 | 5/2003 | Agren et al. |
| 2003/0094502 A1 | 5/2003 | Andersson et al. |
| 2003/0129360 A1 | 7/2003 | Derand et al. |
| 2003/0143114 A1 | 7/2003 | Andersson et al. |
| 2003/0156763 A1 | 8/2003 | Soderman |
| 2003/0173650 A1 | 9/2003 | Larsson et al. |
| 2003/0211012 A1 | 11/2003 | Bergstrom et al. |
| 2003/0213551 A1 | 11/2003 | Derand et al. |
| 2003/0231312 A1 | 12/2003 | Sjoberg et al. |
| 2004/0005634 A1 | 1/2004 | Patz et al. |
| 2004/0055136 A1 | 3/2004 | Ohman et al. |
| 2004/0058408 A1 | 3/2004 | Thomas et al. |
| 2004/0096867 A1 | 5/2004 | Andersson et al. |
| 2004/0099310 A1 | 5/2004 | Andersson |
| 2004/0120856 A1 | 6/2004 | Andersson et al. |
| 2004/0131345 A1 | 7/2004 | Kylberg et al. |
| 2004/0202579 A1 | 10/2004 | Larsson et al. |
| 2005/0019819 A1 | 1/2005 | Tooke et al. |
| 2005/0042770 A1 | 2/2005 | Derand et al. |
| 2005/0129800 A1 | 6/2005 | Ohman et al. |
| 2005/0141344 A1 | 6/2005 | Ekstrand et al. |
| 2005/0153431 A1 | 7/2005 | Andersson et al. |
| 2005/0153432 A1 | 7/2005 | Andersson et al. |
| 2005/0153433 A1 | 7/2005 | Andersson et al. |
| 2005/0153434 A1 | 7/2005 | Andersson et al. |
| 2005/0179901 A1 | 8/2005 | Ostlin et al. |
| 2005/0186685 A1 | 8/2005 | Kange et al. |
| 2005/0202471 A1 | 9/2005 | Tooke et al. |
| 2005/0214442 A1 | 9/2005 | Larsson et al. |
| 2005/0277195 A1 | 12/2005 | Holmquist et al. |
| 2005/0279925 A1 | 12/2005 | Andersson et al. |
| 2006/0002825 A1 | 1/2006 | Derand et al. |

FOREIGN PATENT DOCUMENTS

| | | |
|---|---|---|
| DE | 29500587 | 5/1996 |
| EP | 0241140 B1 | 10/1987 |
| EP | 0282840 A2 | 9/1988 |
| EP | 0745856 A2 | 12/1996 |
| EP | 0977032 A1 | 2/2000 |
| FR | 2657879 | 8/1991 |
| WO | WO-93/22053 | 11/1993 |
| WO | WO-93/22054 | 11/1993 |
| WO | WO-93/22055 | 11/1993 |
| WO | WO-93/22058 | 11/1993 |
| WO | WO-9426413 | 11/1994 |
| WO | WO-96/06354 | 2/1996 |
| WO | WO-96/07919 | 3/1996 |
| WO | WO-96/14933 | 5/1996 |
| WO | WO-96/15450 | 5/1996 |
| WO | WO-9614933 A1 | 5/1996 |
| WO | WO-9707993 A1 | 3/1997 |
| WO | WO-97/21090 | 6/1997 |
| WO | WO-9721090 A1 | 6/1997 |
| WO | WO-97/45730 | 12/1997 |
| WO | WO-98/07019 | 2/1998 |

| | | |
|---|---|---|
| WO | WO-9807019 A1 | 2/1998 |
| WO | WO-98/15356 | 4/1998 |
| WO | WO-98/22625 | 5/1998 |
| WO | WO-98/38510 | 9/1998 |
| WO | WO-98/39645 | 9/1998 |
| WO | WO-98/52691 A1 | 11/1998 |
| WO | WO-99/58245 | 11/1999 |
| WO | WO-00/25921 | 5/2000 |
| WO | WO-00/40750 | 7/2000 |
| WO | WO-00/62042 | 10/2000 |
| WO | WO-01/02737 | 1/2001 |
| WO | WO-01/30500 | 5/2001 |
| WO | WO-2004/067444 | 8/2004 |
| WO | WO-2004/083108 | 9/2004 |
| WO | WO-2004/083109 | 9/2004 |
| WO | WO-2004/103890 | 12/2004 |
| WO | WO-2004/106926 | 12/2004 |

OTHER PUBLICATIONS

Handique et al., "Microfluidic flow control using selective hydrophobic patterning," SPIE Proceedings, vol. 3224, pp. 185-195, 1997.
U.S. Appl. No. 09/830,475, Inventor: Moineau, Filed Sep. 24, 2001.
U.S. Appl. No. 09/958,577, Inventor: Ulfendahl, Filed Apr. 7, 2000.
U.S. Appl. No. 10/070,912, Inventor: Ohman, Filed Mar. 13, 2002.

MICROFABRICATED APPARATUS FOR CELL BASED ASSAYS

This application is a continuation of U.S. application Ser. No. 10/650,412, filed Aug. 28, 2003, now abandoned, which is a continuation of U.S. application Ser. No. 09/673,169, filed Nov. 17, 2000, now U.S. Pat. No. 6,632,656, which is the National stage Application of International Application No. PCT/GB99/00954, filed on Mar. 17, 1999, which claims priority to Great Britain Application 9808836.2 filed Apr. 27, 1998.

The present invention relates to cell based assays. In particular the invention relates to a microfabricated apparatus for performing cell growth and cell based assays and to methods for performing such assays.

The current focus in high throughput screening applications towards the screening of increasing numbers of compounds is being driven by the twin technologies of combinatorial chemistry and genomics, in order to produce new potential drug targets and novel candidate drugs as potential therapeutic compounds. The primary screening process has been addressed by the development of high throughput screening assay processes and assay miniaturisation utilising the microtitre well plate format with 384, 864, 1536 or greater miniaturised wells. Miniaturised assays are capable of allowing throughput levels of over 100,000 tests/day in primary screening. At this level of throughput, a primary screen might be expected to yield 100-1000 'hits' per day. Each of these putative drugs is required to undergo further refined screening and testing in a variety of assays in order to investigate the biological compatibility of the compound. Such assays include bioavailability, metabolism and toxicology, and they are carried out predominantly using cultured cell lines. In comparison with assays used in the primary screening process, secondary screening assays have a much higher level of complexity and more stringent requirements, both in the mechanics of the assay and in the information generated. There is a requirement in the art for secondary screening assay methodologies which are capable of handling both the increasing rate of putative drug lead generation and the generation of biological data concerning the drug candidate. In addition, development of assays yielding higher information content have the potential to increase the level of characterisation of a lead drug during the screening phase of drug development.

Microfabricated devices have been described previously which are suitable for use in miniaturized biological analyses. For example, WO 96/15450 discloses a device which comprises an etched glass structure with a collection of chambers connected by a micro-channel and enclosed by a glass cover plate. Devices have been described by Wilding et al., for example in WO 93/22058, which discloses a mesoscale device for amplifying DNA by PCR, the device consisting of a number of chambers connected by a channel. WO 93/22055 and WO 93/22053 relate to devices for analysing a fluid cell-containing sample comprising a mesoscale flow system with entry port for capture and/or lysis of cells in biological fluids, or containing a binding moiety for specifically binding an analyte, where the analyte may be an intracellular component in a cell in a sample, or a cell population in a sample. The above devices are concerned with the measurement or detection of cells or cellular analytes in cells introduced into the device immediately prior to analysis. They are not described for use in cell culture or growth, nor for use in the study of cellular responses to agents under test. Moreover, they do not describe or permit the use of adherent cultured cells.

There is a requirement for a device capable of providing an environment which supports the long term survival of cultured cells, coupled with means to utilise cells cultured within the device for secondary drug screening or other studies.

In one aspect, the present invention provides apparatus microfabricated for performing cell growth and cell based assays in a liquid medium, said apparatus comprising:
a) a base plate supporting a plurality of micro-channel elements, each comprising a cell growth chamber, an inlet channel for supplying liquid sample thereto and an outlet channel for removal of liquid sample therefrom;
b) a cover plate positioned over said base plate said cover plate extending over said elements so as to define said chambers and connecting channels; said cover plate being supplied with holes to provide access to said channels; and
c) means, incorporated in said cell growth chambers, for cell attachment and cell growth.

In a second aspect of the invention there is provided a method for studying the effect of a test substance on a cellular activity or physical parameter by the use of the apparatus as defined, which method comprises:
a) providing a suspension of cells in a fluid medium;
b) introducing said cells into said apparatus and causing said cells to be transported to one or more cell growth chambers in said apparatus;
c) providing one or more samples of test substances whose effect upon the cells is to be measured under conditions so as to cause said cells to be exposed to said substances;
d) determining the effect of the test substances on said cells by means of optical detection.

Preferably the method for studying the effect of a test substance includes the step of culturing cells adhering to a surface within the apparatus prior to the introduction of the test substances. Preferably there are provided following step c) one or more assay reagents and dispersing the reagents to one or more reaction chambers in the apparatus.

In a further aspect of the present invention there is provided a method for measuring a cellular analyte by the use of the apparatus as defined, which method comprises:
a) providing a suspension of cells containing an analyte to be measured in a fluid medium;
b) introducing cells into the apparatus and causing the cells to be transported to one or more cell growth chambers in the apparatus;
c) allowing cells to grow;
d) providing one or more assay reagents and dispersing the reagents to one or more chambers in the apparatus;
e) measuring the cellular analyte by optical means.

In order that the invention may be better understood, several embodiments will now be described by way of example only and with reference to the accompanying drawings in which.

Figure 1A:
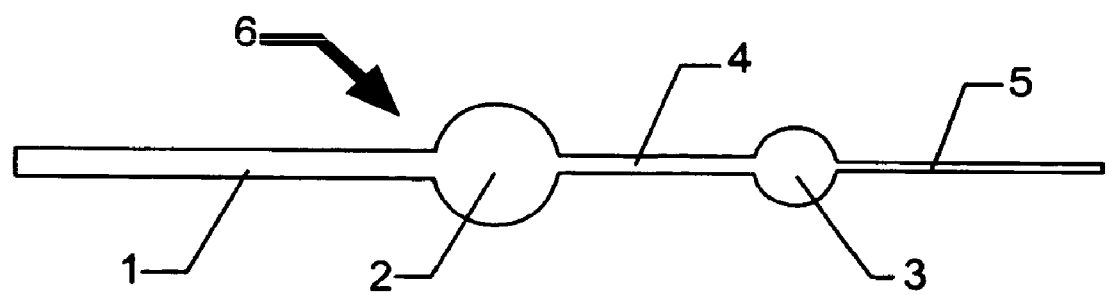
FIG. 1a is a diagrammatic representation in plan of an individual micro-channel element of the microfabricated apparatus for performing cell growth and cell based assays.
Figure 1B:
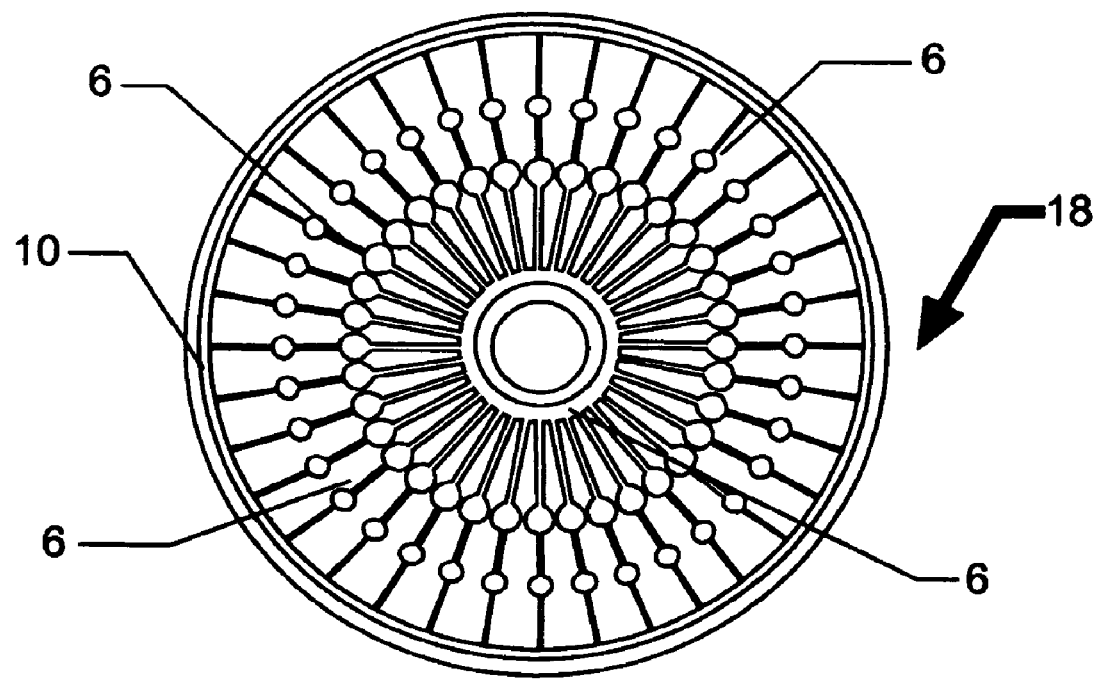
FIG. 1b is a sectional view of a microfabricated disc including a plurality of assay elements for performing cell growth and cell based assays according to the present invention.

Referring to FIG. 1b, the apparatus of the present invention comprises a rotatable disc (18) microfabricated to provide a sample introduction port (not shown) located towards the centre of the disc and connected to an annular sample reservoir (9) which in turn is connected to a plurality of radially dispersed micro-channel assay elements (6) each of said micro-channel elements comprising a cell growth chamber, a sample inlet channel and an outlet channel for removal of liquid therefrom and a cover plate positioned onto said disc so as to define closed chambers and connecting channels. Each micro-channel element is connected at one end to the central sample reservoir (9) and at the opposing end to a common waste channel (10).

Each of the radially-dispersed micro-channel elements (6) of the microfabricated apparatus (shown in FIG. 1a) comprises a sample inlet channel (1) connected at its left hand-end end to the reservoir (9), a cell growth chamber (2) for performing cell growth and connected through a channel (4) to an assay chamber (3) and an outlet channel (5) connected at its right-hand end to the waste channel (10).

Figure 2:
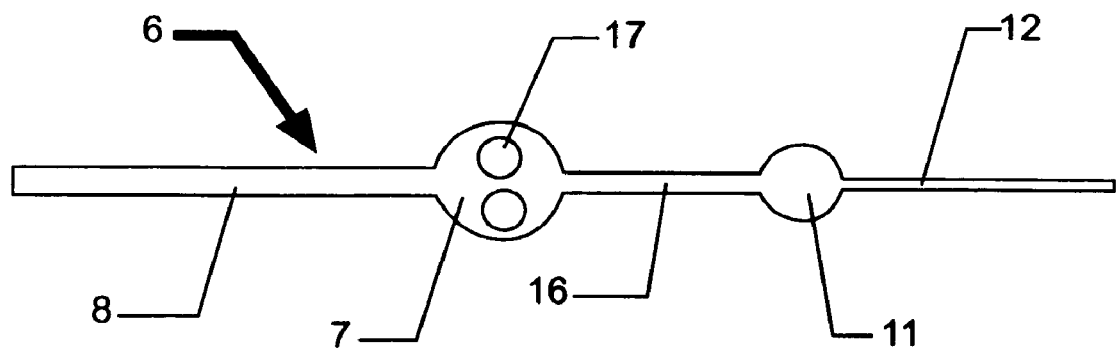
FIG. 2 represents an alternative configuration of an individual assay element of the microfabricated apparatus for use with cells growing on the surface of microcarrier beads.

In an alternative format of the present invention as shown in FIG. 2, the micro-channel elements (6) are modified to permit the use of the apparatus with cells growing on the surface of microcarrier beads (17). Thus, each micro-channel element (6) comprises a sample inlet channel (8) connected at its left-hand end to the sample reservoir (9), a cell growth chamber (7) connecting through a channel (16) to an assay chamber (11), and an outlet channel (12) leading to the common waste channel (10).

Figure 3:
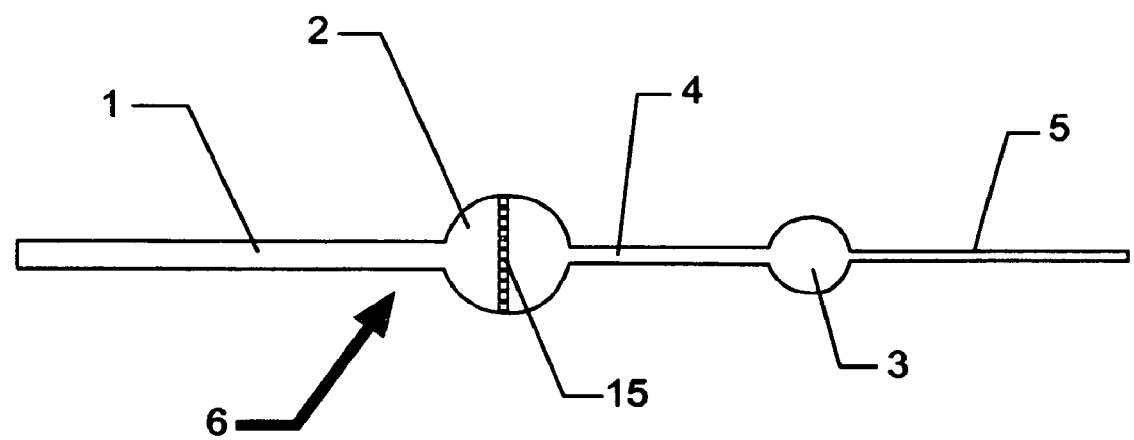
FIG. 3 represents a further configuration of an individual assay element of the microfabricated apparatus in which means are provided for preventing or impeding the passage of cells in the cell growth chamber.

With reference to FIG. 3, in a further embodiment of the apparatus, the cell growth chamber (2) may be provided with raised moulded structures disposed on the base portion of the cell growth chamber to form pillars (15), such that they form a barrier to the flow or passage of cells arriving in the cell growth chamber (2) through the inlet channel (1), while allowing the passage of liquid. These structures are of dimensions chosen to provide gaps between the structures which are too narrow to allow passage of cells carried as a suspension in liquid moving in the device, but which are sufficiently large to allow cells growing on the surface of the cell growth chamber (14) to migrate through the barrier by extension of cell processes between the barrier and subsequent cytokinesis. Suitable dimensions for the gaps between the raised pillars (15) formed in the cell growth chambers are between 5 and 50 µm, depending upon the cell type and cell size selected for capture.

Preferably, each micro-channel element (6) shown in FIG. 3 additionally includes one or more assay chambers for performing assays involving cellular constituents and being connected in line between said cell growth chamber (2) and said outlet channel (5).

Suitably the disc (18) is of a one- or two-piece moulded construction and is formed of an optionally transparent plastic or polymeric material by means of separate mouldings which are assembled together to provide a closed structure with openings at defined positions to allow loading of the device with liquids and removal of waste liquids. In the simplest form, the device is produced as two complementary parts, one or each carrying moulded structures which, when affixed together, form a series of interconnected micro-channel elements within the body of a solid disc. Alternatively the micro-channel elements may be formed by micro-machining methods in which the micro-channels and chambers forming the micro-channel elements are micro-machined into the surface of a disc, and a cover plate, for example a plastic film, is adhered to the surface so as to enclose the channels and chambers.

To provide cultured cells with means for obtaining oxygen for metabolism and to permit use of $CO_2$-buffered media, one or more components of the device may be constructed from a gas permeable plastic, film, polymer, or membrane. Suitably, the gas permeable plastic, film, polymer, or membrane is formed from silicone polymers, such as polydimethylsiloxane, or from polyurethane, polytetrafluoroethylene or other gas permeable plastic materials. In addition, means (not shown) are preferably provided for sealing the openings in the closed structure to prevent evaporation of liquid during use, whereby such means seal the openings without interfering with gas exchange to the cell growth medium. Sealing can be accomplished by use of a further layer of gas permeable material across the whole device, or by use of a non-permeable material applied locally to the openings only, leaving the remainder of the gas permeable material exposed to the local atmosphere.

Suitable plastic or polymeric materials for forming the cell growth chamber and micro-channels are preferably selected to have hydrophobic properties, where the surface of the plastic or polymer can be additionally selectively modified by chemical or physical means to alter the surface properties to confer a desired property, for example, compatibility with cell growth, cell attachment and the attachment of biomolecules by covalent or non-covalent means. Preferred plastics are selected from polystyrene and polycarbonate.

Alternatively, the cell growth chamber and micro-channels may be constructed from plastic or polymeric materials which are selected to have hydrophilic properties. The surface of the plastic or polymer can be additionally selectively modified by chemical or physical means to alter the surface properties so as to produce localised regions of hydrophobicity within the chambers and/or microchannels to confer a desired property. By this means, for example, hydrophobic barriers or valves may be provided to control liquid flow within the apparatus. Preferred plastics are selected from polymers with a charged surface, suitably chemically or ion-plasma treated polystyrene, polycarbonate or other rigid transparent polymers.

The micro-channel elements (6) are dispersed radially around the disc (18) and connected to a common centre port. The channels 1, 4, 5, 8, 12, and 16 are of a dimension compatible with movement of cells along the channels. Suitably, the channels and chambers may be of any cross-sectional shape, such as square, rectangular, circular, trapezoid and triangular. Suitably, the cell growth chamber (2) is sized to give a floor area between 100 $\mu m^2$ and 1,000,000 $\mu m^2$, preferably between 1000 $\mu m^2$ and 1,000,000 $\mu m^2$ and most preferably between 10,000 $m^2$ and 1,000,000 $\mu m^2$. The plastic or polymer surface of the cell growth chamber may be selectively treated or modified to permit cell attachment and/or growth. Treatment preferably involves exposure to intense UV light to modify the polymer surface or alternatively the use of high voltage plasma discharge using known techniques (see Amstein, C. F. and Hartmann, P. A., J. Clin. Microbiol., 2, 1, 46-54 (1975)) to create a negatively charged surface suitable for cell growth and attachment and (if required) for assay purposes. Cell attachment may be further improved by the application of additional coatings to the surface of the cell growth chamber, eg. polylysine, collagen, fibronectin.

As already mentioned, in the preferred aspect of the invention, each of the micro-channel elements (6) is further provided with an assay chamber (3) which is located in line between the cell growth chamber (2) and the outlet channel (5), for performing assays involving cellular constituents. The assay chamber is sized proportionally to the volume of the cell growth chamber (2) to allow collection and/or capture of soluble analytes which may be derived from the cultured cells under study. Suitably, the volume of the assay chamber (3) is between twice and one tenth of the volume of the cell growth chamber (2). Advantageously, the channel (4) which connects the cell growth chamber and the assay chamber is characterised by having hydrophobic walls and a cross-sectional area which is smaller than the channel (1) upstream of the cell growth chamber. Suitably, channel (4) has a cross-sectional area of between 0.99 and 0.01 times that of the inlet channel (1). Suitably, the outlet channel (5) is characterised by having hydrophobic walls and a cross-sectional area of between 0.99 and 0.01 times that of channel (4). In this way, liquid flow in the micro-channel elements can be controlled by application of a defined centrifugal force to cause the liquid to flow in a channel of a defined cross-sectional area, wherein the same force is insufficient to cause the liquid to flow in further linked channels of lesser cross-sectional area, this having the effect of stopping the liquid flow at a desired position in the micro-channel element.

In an alternative means of controlling liquid flow, channel (1) and channel (4) are constructed with the same cross-sectional area, but the surface of each of the channels may be selectively modified by chemical or physical means to confer a different degree of hydrophobicity on that channel. For example, channel (4) downstream of the cell growth chamber (2) may be treated to have a higher hydrophobicity than the channel (1) upstream of the cell growth chamber. By this means, application of a defined force to liquid in channel (1), sufficient to cause liquid to move down this channel will be insufficient to cause that liquid to enter the second channel (4) of higher hydrophobicity, this having the effect of stopping the liquid flow at a desired position in the micro-channel element. Suitable means for selectively modifying the hydrophobicity of the surface of the channels include exposure of defined areas to ionizing or electromagnetic radiation or ion plasma through a mask, or by application of a hydrophobic material or ink by screen printing or other means of localized application.

The means of controlling liquid flow within the apparatus as described above may be used alone or in combination as required, in order to confer the desired control of liquid flow in connected chambers and channels within the micro-channel element. If used in combination, the methods may be used sequentially, for example where a change in cross-sectional area is followed by a change in hydrophobicity, forming two sequential points of liquid flow control. Alternatively, the methods may be used coincidentally, in which a change in cross-sectional area of a channel is accompanied by a change in hydrophobicity of that channel, the combination being used to confer a degree of control over liquid flow not attainable using a single means.

The inner surface of the assay chamber may be coated with one or more ligands capable of specifically binding an analyte of interest by covalently or non-covalently linking the ligand to the surface. Examples of ligands suitable for the purpose include: biotin, streptavidin, protein A, antibodies, lectins, hormone receptors, nucleic acid probes, DNA binding proteins and the like.

The apparatus and method can be used for the growth of cells and the detection and measurement of cellular activity, cellular parameters and biochemical processes, for example cellular metabolism, cell viability, reporter gene expression, using non-invasive techniques, that is techniques which do not compromise the integrity or viability of cells. Alternatively, the apparatus may be used in the detection and measurement of cell-derived products, which have been released or otherwise excreted from cells, such as peptide hormones, second messengers, etc. By use of the apparatus shown in FIG. 3, the apparatus permits studies of cell migration in response to chemical or physical stimuli, for example chemotaxis, wherein a chemoattractant substance is placed on one side of a barrier and cells placed on the opposite side of the barrier are observed to penetrate the barrier in moving toward the chemoattractant.

The invention may be used with any cell type that can be cultured on standard tissue culture plastic-ware. Such cell types include all normal and transformed cells derived from any recognised source with respect to species (eg. human, rodent, simian), tissue source (eg. brain, liver, lung, heart, kidney skin, muscle) and cell type (eg. epithelial, endothelial). In addition, cells which have been transfected with recombinant genes may also be cultured using the invention. There are established protocols available for the culture of diverse cell types. (See for example, Freshney, R. I., Culture of Animal Cells: A Manual of Basic Technique, $2^{nd}$ Edition, Alan R. Liss Inc. 1987). Such protocols may require the use of specialised coatings and selective media to enable cell growth and the expression of specialist cellular functions. None of such protocols is precluded from use with the apparatus of this invention.

The scale of the device will to a certain extent be dictated by its use, that is the device will be of a size which is compatible with use with eukaryotic cells. This will impose a lower limit on any channel designed to allow movement of cells and will determine the size of cell containment or growth areas according to the number of cells present in each assay. An average mammalian cell growing as an adherent culture has an area of ~300 $\mu m^2$; non-adherent cells and non-attached adherent cells have a spherical diameter of ~10 $\mu m$. Consequently channels for movement of cells within the device are likely to have dimensions of the order of 20-30 $\mu m$ or greater. Sizes of cell holding areas will depend on the number of cells required to carry out an assay (the number being determined both by sensitivity and statistical requirements). It is envisaged that a typical assay would require a minimum of 500-1000 cells which for adherent cells would require structures of 150,000-300,000 $\mu m^2$, i.e. circular 'wells' of ~400-600 $\mu m$ diameter.

The configuration of the micro-channels in the present invention is preferably chosen to allow simultaneous seeding of the cell growth chamber by application of a suspension of cells in a fluid medium to the sample reservoir by means of the sample inlet port, followed by rotation of the disc (18) by suitable means at a speed sufficient to cause movement of the cell suspension outward towards the periphery of the disc by centrifugal force. The movement of liquid distributes the cell suspension along each of the inlet micro-channels (1, 8) towards the cell growth chambers (2, 7). The rotation speed of the disc is chosen provide sufficient centrifugal force to allow liquid to flow to fill the cell growth chamber (2, 7), but with insufficient force for liquid to enter the restricted channel (4, 16) of smaller diameter on the opposing side of the cell growth chamber.

Once rotation has stopped, cells in the suspension can settle under gravity onto the bottom of the cell growth chamber (2, 7) and attach to the treated surface if present. Cells which remain in the channel are unable to attach to the untreated hydrophobic surface and will remain in suspension. Therefore, following an appropriate period of time, chosen to allow cell attachment to take place, the device may be rotated at a higher speed than previously, such that all liquid and unattached cells is caused to move towards the periphery of the disc into the waste channel (10) disposed around the edge of disc. Following clearance of channels of unattached cells, rotation is slowed to the same speed initially used to fill the micro-channel elements and fresh cell culture media is applied to the sample reservoir. By rotation of the disc once more, the cell culture media flows under centrifugal force to fill the micro-channels and the cell growth chambers as previously described. This action leaves the attached cells seeded on the surface of the cell growth chambers covered in fresh culture media suitable for cell growth and for cell based assays.

In the apparatus of FIG. 2, the beads (17) provide a large surface area for cell attachment and growth in a relatively small volume of liquid. In the device described herein, the beads (17) perform two functions; firstly they provide a surface for the attachment and growth of cells, so removing the need to provide a cell-growth compatible surface within the disc allowing a wider range of materials to be used for construction, and secondly they provide a larger physical carrier for cells which allows channels within the device to be easily designed to prevent access of cells. In the preferred embodiment, each element comprises a cell growth chamber (2, 7), an analysis chamber (3, 11), and a waste chamber (10) which are arranged radially about the centre of the disc and connected to a common port in the centre of the disc.

Following the addition of cell samples to the apparatus, their attachment and subsequent cell growth, reagents and samples for assay may be introduced into the sample reservoir (9) through the sample inlet port. Reagents to be supplied to all micro-channel elements may be introduced as described hereinbefore for seeding with cells, that is by applying a solution containing reagents to the central port and rotating the disc so as to cause distribution of the reagent to all micro-channels, cell growth chambers and assay chambers. The application of specific samples to specific wells may be achieved by pipetting small volumes of liquid as discrete drops into the central well directly adjacent to the opening of the inlet channel leading to the cell growth chamber which is to receive the sample. This may be achieved, for example, by the use of a piezo-electric dispensing device (not shown), whereby dispensing of droplets of liquid from the device is synchronised with the speed of rotation of the disc (18) such that, at an appropriate combination of dispensing drop frequency and rotation speed of the disc, individual droplets of liquid can be caused to impinge on the surface of the disc and can be caused to be transported by centrifugal force into an adjacent inlet channel (1, 8) and to mix with liquid present in the cell growth chamber (2, 7).

Alternatively liquids may be pipetted as discrete drops onto the hydrophobic surface of a stationary disc (18), rotation of the disc being used to move these drops of liquid into the appropriate inlet channel and so to the cell growth chamber. By these means, all reagents and samples may be provided to the cell chamber in the desired order and proportions to perform the assay.

Once the liquid manipulations of the assay have been performed it is necessary to perform a detection procedure to measure the result of the assay, typically by measuring the signal emitted by a fluorescent, chemiluminescent or other labelling moiety. The device as shown in FIG. 1b is configured to allow two means of detection of the assay signal. Firstly, the assay signal may be measured in-situ in the cell growth chamber. Such a signal would be typified by the measurement of the product of a reporter gene within the cells, e.g. fluorescence from GFP.

Alternatively, it may be desirable to measure cell-derived products or analytes, for example by immunochemical or other specific binding assay methods, in the absence of cells cultured in the apparatus, so as to avoid interference in measurement. In this case, the apparatus is provided with a second chamber, ie. the assay chamber (3, 11) disposed closer to the periphery of the disc and connected to the cell growth chamber (2, 7). The assay chamber is connected to the peripheral waste channel (10) by a narrow channel (5, 12), this channel having a smaller diameter than that (4, 16) connecting the assay chamber to the cell growth chamber. The differential in diameters between chambers allows, under controlled conditions of rotation and centrifugal force, as discussed above, liquid to be moved from the cell growth chamber to the assay chamber. For example, by this process, an analyte is moved from the cell growth chamber into the assay chamber where the analyte is subject to affinity capture by a ligand attached to the wall of the assay chamber. This process therefore provides a means of moving a cell-derived analyte, which has been released or otherwise excreted from cells, away from the cellular environment, immobilising the analyte within the assay chamber by means of a specific binding partner for binding to the analyte, and allowing subsequent additions of reagents and processing to permit the detection of the analyte.

Optionally, at least one of the reagents for use in an assay method utilising the apparatus may be labelled with a detectable label by covalent or non-covalent attachment. Suitable detectable labels may be selected from fluorescent labels, chemi-luminescent labels, bio-luminescent labels, enzyme labels and radioactive labels. Suitable fluorescent labels for tagging reagents according to the method of the invention may be selected from the general categories of fluorescent dyes, including, but not limited to, fluoresceins, rhodamines, cyanine dyes, coumarins, and the BODIPY groups of fluorescent dyes. Examples of bioluminescent detectable labels are to be found in the fluorescent reporter proteins, such a Green Fluorescent Protein (GFP) and aequorin. Alternative labels for providing a detectable signal can be fluorescence energy transfer labels.

Once the assay has been completed, measurement of the signal may be achieved by means appropriate to the labelling molecule or moiety used in the assay and is typically by optical means. For example, luminescence emitted from cells or from a fluorescent labelled assay reagent may be detected in the microfabricated apparatus by the use of imaging apparatus incorporating a CCD camera, or by the use of a fluorimeter. Detection of emitted fluorescence may be achieved through the body of the disc (18) where the disc is wholly constructed of a transparent material or alternatively through windows of transparent material which have been fabricated into the body of the disc.

As an alternative to non-radioactive detection, the apparatus of the present invention may be used in conjunction with radioactive detection utilising the scintillation proximity technique. For example, scintillant-containing beads may be introduced into the apparatus. Alternatively the microfabricated apparatus of the invention may have incorporated a scintillant containing layer into or onto an interior surface of the cell growth chamber (2, 7) and/or the assay chamber (3, 11). The region of the apparatus containing the scintillant beads or scintillant surface is preferably optically transparent so as to enable the material to transmit light at a given wavelength with optimum efficiency. The scintillant-containing region can be composed of any transparent material containing scintillant, eg. a scintillant glass based on lanthanide metal-containing compounds, or a plastic material such as polystyrene or polyvinyltoluene, into which is incorporated the scintillant substance.

Suitable scintillant substances can include aromatic hydrocarbons such as p-terphenyl, p-quaterphenyl and their derivatives, and derivatives of oxazoles and 1,3,4-oxadiazoles, for example, 2-(4-t-butylphenyl)-5-(4 biphenylyl)-1,3,4-oxadiazole and 2,5-diphenyloxazole. A wavelength shifter such as 1,4-bis(5-phenyl-2-oxazolyl)benzene, or 9,10-diphenylanthracene, may also be included.

A binding moiety such as one member of a specific binding pair may be immobilised onto the surface of the bead or scintillant layer so as to specifically bind with an analyte which may be derived from cells used in the assay process. Suitable specific binding pair members with which the invention is useful include biotin, streptavidin, protein A, antibodies, lectins, hormone receptors, nucleic acid probes, DNA binding proteins and the like. It is to be understood that either member of the specific binding pair may be attached and immobilised for binding to a complementary member of the specific binding pair.

Typical radioistopes that may be used to label the assay reagent include those commonly used in biochemistry such as [$^3$H], [$^{125}$I], [$^{35}$S] and [$^{33}$P] but does not preclude the use of other isotopes. Detection methodologies based on scintillation proximity are well known (see for example U.S. Pat. No. 4,568,649, Bertoglio-Matte, J.). Detection may utilise a number of modalities to be combined to allow all assays to be measured simultaneously or in rapid succession. Alternatively an appropriate imaging format may provide suitable detection means for both radioactive and non-radioactive assays utilising the apparatus.

In some uses, some assay areas will be redundant; that is, not all elements of the apparatus will be used every time. It is envisaged that the user will decide what type of assays it is required to perform and then select appropriate control means for directing liquid flow within the apparatus. Consequently, such structures will be compatible with a range of assay procedures and protocols which require different complexities of fluid movement. For example, detection of a GFP linked reporter gene will require a simple well structure to allow measurement of fluorescence. In contrast, measurement of an analyte secreted from cells, for example the measurement of a cytokine by immunoassay, or measurement of cellular mRNA following lysis, will require a more complicated structure to separate the cells from the secreted analyte prior to the analysis of that analyte The invention is further illustrated by reference to the following examples.

EXAMPLE 1

A stock culture of HeLa cells was grown in Dulbecco's Modified Eagles Medium (DMEM) supplemented with 10% calf serum and L-glutamine in a plastic flask using standard tissue culture conditions. Cells were harvested by trypsinisation and the resulting suspension concentrated by centrifugation to give a cell concentration of $10^7$ cells/ml. Aliquots of the cell suspension (1 μl) were applied to openings in the surface of a microfabricated structure of the type shown in FIG. 1, produced by injection moulding, with internal channels of depth 50 μm and width 100 μm.

The cells suspension was moved along the inlet channels within the disc to circular cell growth chambers of depth 50 μm and diameter 500 μm and the cells allowed to attach and grow. Following incubation for 48 hours in a tissue culture incubator (37° C./95% RH) the cells were examined for cell density, morphology and viability. Visible examinations by phase contrast microscopy showed cell populations growing in microstructures to have the same density and morphology as control cultures grown from the same parent stock and maintained in standard tissue culture plasticware. Cells were subsequently tested for viability using a commercial test kit (LIVE/DEAD Viability Kit, Molecular Probes, Oregon, L-3224) by flushing growth medium from the cells within the device, washing the cells with a phosphate buffered saline solution (PBS) and introducing a solution of the fluorescent assay reagents into the cell growth chambers. Subsequent examination by fluorescent microscopy showed that cells growing in microstructures had maintained a cell viability of >95%, comparable with control cells grown under standard tissue culture conditions.

EXAMPLE 2

A microfabricated plastic disc of the type shown in FIG. 1, produced by injection moulding which contained a number of radial internal channels of depth 50 μm and width 100 μm was selectively surface modified by exposure to a 500 W UV lamp at a distance of 20 cm for 30 minutes through a metal mask such that UV light impinged on the surface only on regions defined by the mask.

A stock culture of HeLa cells was grown in Dulbecco's Modified Eagles Medium (DMEM) supplemented with 10% calf serum and L-glutamine in a plastic flask using standard tissue culture conditions. Cells were harvested by trypsinisation and the resulting suspension concentrated by centrifugation to give a cell concentration of $10^7$ cells/ml. Aliquots of the cell suspension (1 μl) were applied to openings in the surface of the device and cells moved along the channels by rotation about the disc axis (1000 rpm for 30 seconds). Following incubation for 18 hours in a tissue culture incubator (37° C./95% RH) cells were examined by phase contrast microscopy. Cells were found to be preferentially growing in regions of the disc previously exposed to UV light, cells in other regions were observed to be sparser and less well attached. The disc was then rotated at 1000 rpm for 30 seconds and cells re-examined. Following spinning cells in UV exposed areas were observed to have remained attached to the plastic surface and remained morphologically identical to control cells; in contrast cells on non-exposed surfaces were totally removed by the centrifugal force generated by the spinning disc.

EXAMPLE 3

HeLa cells grown and harvested as described above were introduced into the device of Example 2 into micro channels which contained moulded pillars of various dimensions dispersed in the channels so as to act as barriers to cell movement in the channels. A suspension of cell was introduced into the channels and the structure incubated for 18 hours to allow the cells to settle and grow. Subsequent examination revealed that in channels where the gaps between pillars were 10×60 μm or greater cells were observed to have moved freely past the barriers. In contrast where gaps between pillars were 10×20 μm or less, cells were prevented from passing the barrier when transported by liquid flow in suspension. However on subsequent incubation and growth cells were observed to migrate past such barriers by slow deformation. Such barrier structures may prove useful for study of cell movement or migration in response to chemical or physical stimuli.

EXAMPLE 4

HeLa cells transfected to yield stable expression of a Cal-reticulin-GFP fusion protein were introduced into a moulded apparatus of the type shown in FIG. 1, supporting channels of 100 μm width and 100 μm depth connected to circular chambers of 600 μm and 1000 μm diameter and 100 μm depth. Cells were incubated for 18 hours in a tissue culture incubator and examined by confocal fluorescence microscopy. Cells grown in microfabricated structures showed the same level of GFP expression as control cells grown under conventional tissue culture conditions.

EXAMPLE 5

HeLa cells were grown and introduced into a microfabricated disc as described in Example 1. Following incubation for 18 hours growth medium was removed from cells and replaced with media containing different concentrations of the membrane permeabilising agent digitonin in the range 0-0.2 mg/ml (w/v) and cells incubated in the presence of digitonin for 10 minutes. Thereafter the viability of the cells was measured as described in Example 1. Results were found to be equivalent to cells exposed to the same dose range of digitonin in a microtitre plate based assay.

The invention claimed is:

1. An apparatus microfabricated for performing cell growth in a liquid medium, said apparatus comprising:
   a) a base plate supporting a plurality of micro-channel elements, each comprising a cell growth chamber, an inlet channel, and an outlet channel;
   b) a cover plate positioned over said base plate said cover plate extending over said elements so as to define said chambers and channels; and
   c) a hydrophobic valve in at least one of said chambers or said channels that is defined by positioning said cover plate over said base plate, wherein said valve comprises a localized region of hydrophobicity within said chamber or said channel, wherein the hydrophobic valve prevents liquid flow until subjected to the application of a defined force,
   wherein at least some of said micro-channel elements each comprises one or more assay chambers for performing assays involving cellular constituents and connected in line between said cell growth chamber and said outlet channel.

2. The apparatus of claim 1 further comprising means, incorporated in said cell growth chamber, for cell growth, wherein one or more components of the apparatus are constructed of a gas permeable film or membrane such that $CO_2$-buffered media can be used in the cell growth chamber and gas may permeate to and from the cells for their metabolism during growth.

3. The apparatus of claim 2, wherein said means for cell growth comprises at least a portion of a surface of said cell growth chamber that is treated to allow for cell attachment.

4. The apparatus of claim 3, wherein said surface is negatively charged surface.

5. The apparatus of claim 3, wherein said surface comprises a coating of polylysine, collagen or fibronectin.

6. The apparatus of claim 2, wherein said means for cell growth comprises one or more microcarrier beads located in said cell growth chamber, wherein each of said microcarrier beads provides for cell attachment.

7. The apparatus of claim 1 further comprising a suspension of cells to be grown in each of said cell growth chambers.

8. The apparatus of claim 7, wherein said cells require attachment to said cell growth chambers for growth.

9. The apparatus of claim 1, wherein said base plate comprises a rotatable disc which is microfabricated to provide a sample introduction port located towards the center of the disc and connected to an annular sample reservoir, and wherein said micro-channel elements are radially dispersed on said disc with their respective input channels connected to receive sample from said reservoir.

10. The apparatus of claim 1, wherein said cover plate is fabricated from a gas permeable plastic material.

11. The apparatus of claim 10, wherein the plastic material is a silicone polymer, polyurethane or polytetrafluoroethylene.

12. The apparatus of claim 11, wherein the silicone polymer is polydimethylsiloxane.

13. The apparatus of claim 1, wherein said cell growth chamber comprises raised moulded features disposed on the base portion of said cell growth chamber to form pillars.

14. The apparatus of claim 1, wherein the cross-sectional area of said inlet channel is greater than that of said outlet channel.

15. The apparatus of claim 14, wherein the cross-sectional area of said outlet channel is between 0.99 and 0.01 times that of said inlet channel.

16. The apparatus of claim 1, wherein each assay chamber is connected to each other and to said cell growth chamber by an intermediate channel in the order of: inlet channel, cell growth chamber, intermediate channel, assay chamber, outlet channel, and wherein the cross-sectional areas of the respective channels reduce progressively from the inlet channel to the outlet channel.

17. The apparatus of claim 16, wherein the cross-sectional area of each intermediate channel and the outlet channel is between 0.99 and 0.01 times that of the immediately preceding upstream channel.

18. The apparatus of claim 16, wherein there is provided in or on an interior surface of one or more of said chambers a layer comprising a scintillant substance.

19. The apparatus of claim 18, wherein the layer comprising a scintillant substance comprises a binding moiety bound thereto, said binding moiety being a member of a specific binding pair selected from the group consisting of biotin, streptavidin, protein A, antibodies, lectins, hormone-receptors, nucleic acid probes, and DNA-binding proteins.

* * * * *